United States Patent [19]

Ryan et al.

[11] Patent Number: 4,645,861

[45] Date of Patent: Feb. 24, 1987

[54] 3-SULFONYLAMINO-4-AMINO PHENYL ACYL DERIVATIVES

[75] Inventors: Charles W. Ryan; Bruce A. Slomski, both of Indianapolis, Ind.

[73] Assignee: Eli Lilly and Company, Indianapolis, Ind.

[21] Appl. No.: 856,603

[22] Filed: Apr. 25, 1986

Related U.S. Application Data

[62] Division of Ser. No. 373,944, May 2, 1982, Pat. No. 4,483,986.

[51] Int. Cl.$^4$ .................. C07C 143/74; C07C 143/77
[52] U.S. Cl. ........................................ 564/99; 564/80

[58] Field of Search ..................................... 564/80, 99

[56] References Cited

U.S. PATENT DOCUMENTS 4,118,742 10/1978 Paget et al. ..................... 548/306

Primary Examiner—Robert W. Ramsuer
Attorney, Agent, or Firm—Charles W. Ashbrook

[57] ABSTRACT

A 4-acyl-o-phenylenediamine is selectively sulfonated on the amino group meta to the acyl group to provide an important intermediate for benzimidazole pharmaceuticals. Some of the intermediates are new to organic chemistry.

4 Claims, No Drawings

3-SULFONYLAMINO-4-AMINO PHENYL ACYL DERIVATIVES

This application is a division of application Ser. No. 373,944, filed May 2, 1982 now U.S. Pat. No. 4,483,986.

BACKGROUND OF THE INVENTION

1. Field of the Invention

This invention belongs to the field of synthetic organic chemistry, and provides a process for selectively sulfonating one of the two unsubstituted amino groups on a 4-acyl-o-phenylenediamine. The products of the invention are intermediates in the preparation of antiviral benzimidazoles; some of them are new to chemistry.

2. State of the Art

Paget et al., U.S. Pat. No. 4,118,742, teaches the 1-sulfonylbenzimidazoles which are the ultimate products of the present process. The patent teaches a number of variations in the process used to prepare its compounds. In general, it first forms the benzimidazole with the 1-position unsubstituted, and then sulfonates it.

The patent explains (column 5 of the specification) that the sulfonation of the benzimidazole produces a mixture of isomers, which must ordinarily be separated. The problem arises from the fact that the desired antiviral benzimidazoles have a single substituent on the phenyl ring, usually preferably at the 6-position. The molecule is therefore asymmetric. Sulfonation of the benzimidazole by ordinary techniques is equally likely to sulfonate either of the nitrogen atoms, resulting in a mixture of isomers.

The advantage of the present invention, compared to the prior art processes, is that its ability to sulfonate selectively one of the amino groups of the phenylenediamine provides, after ring-closure, an excellent yield of the desired isomeric benzimidazole.

Some of the products of the present invention are taught and claimed by S. J. Dominianni in an application entitled Process of Preparing Chemical Intermediates, filed on the same day as the present application Ser. No. 373,945, now U.S. Pat. No. 4,483,986. Dominianni's process is only functional to make benzoyl compounds, where R is a phenyl group.

SUMMARY OF THE INVENTION

The present invention is a process for preparing a compound of the formula

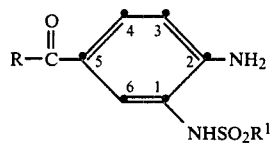

wherein

R is $C_1$–$C_7$ alkyl, $C_3$–$C_7$ cycloalkyl, $C_3$–$C_7$ cycloalkylmethyl, 1-($C_3$–$C_7$ cycloalkyl)ethyl, benzyl, phenyl, or phenyl mono- or disubstituted with $C_1$–$C_4$ alkyl, $C_1$–$C_4$ alkoxy, chloro, bromo, iodo, nitro or trifluoromethyl;

$R^1$ is $C_1$–$C_5$ alkyl, $C_3$–$C_7$ cycloalkyl, phenyl, furyl, thienyl, thiazol-2-yl, 2-acetamido-4-methylthiazol-5-yl, 1,3,4-thiadiazol-2-yl, 2-methyl-1,3,4-thiadiazol-5-yl or $R^2R^3N$-;

$R^2$ and $R^3$ are independently $C_1$–$C_3$ alkyl, or combine with the nitrogen atom to which they are attached to form pyrrolidino, piperidino or morpholino; comprising sulfonating a phenylenediamine of the formula

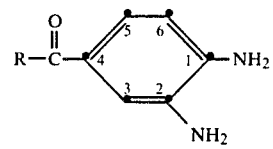

with $BrSO_2R^1$ or $ClSO_2R^1$ in the presence of at least about one mole of a pyridine base chosen from pyridine, the lutidines and the picolines.

The invention also provides the new compounds of the formula

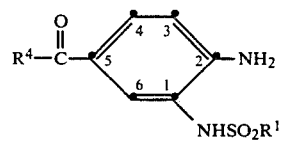

wherein $R^4$ is $C_1$–$C_7$ alkyl, $C_3$–$C_7$ cycloalkyl, $C_3$–$C_7$ cycloalkylmethyl, 1-($C_3$–$C_7$ cycloalkyl)ethyl or benzyl;

$R^1$ is $C_1$–$C_5$ alkyl, $C_3$–$C_7$ cycloalkyl, phenyl, furyl, thienyl, thiazol-2-yl, 2-acetamido-4-methylthiazol-5-yl, 1,3,4-thiadiazol-2-yl, 2-methyl-1,3,4-thiadiazol-5-yl or $R^2R^3N$-;

$R^2$ and $R^3$ are independently $C_1$–$C_3$ alkyl, or combine with the nitrogen atom to which they are attached to form pyrrolidino, piperidino or morpholino.

DESCRIPTION OF THE PREFERRED EMBODIMENT

All temperatures in this document are expressed in degrees Celsius.

The general terms in the above description have their usual meanings in the organic chemical art. The phenyl R group may be unsubstituted, or substituted with one or two groups from the list shown, which groups may be the same or different and may be placed anywhere on the phenyl ring which is not prevented by steric considerations.

The groups $C_1$–$C_4$ alkyl, $C_1$–$C_4$ alkoxy, $C_1$–$C_5$ alkyl, $C_1$–$C_7$ alkyl, $C_3$–$C_7$ cycloalkyl and $C_1$–$C_3$ alkyl include such typical chemical groups as methyl, ethyl, isopropyl, s-butyl, butyl, t-butyl, pentyl, 1-ethylpropyl, 3-methylbutyl, methoxy, ethoxy, isopropoxy, butoxy, i-butoxy, cyclopropyl, cyclobutyl, cyclohexyl, cycloheptyl, hexyl, heptyl, 2,3-dimethylbutyl; 3-ethylpentyl, 1-ethylbutyl and 1,1-dimethylbutyl.

The following group of products of the process of this invention is mentioned to assure that the reader fully understands the invention.

5-benzoyl-$N^1$-methylsulfonyl-o-phenylenediamine 5-(3-methylbenzoyl)-$N^1$-propylsulfonyl-o-phenylenediamine 5-(4-t-butylbenzoyl)-$N^1$-(1-methylbutylsulfonyl)-o-phenylenediamine $N^1$-t-butylsulfonyl-5-(2-methoxybenzoyl)-o-phenylenediamine 5-(3-butoxybenzoyl)-$N^1$-cyclopropylsulfonyl-o-phenylenediamine 5-(2-chlorobenzoyl)-$N^1$-cyclopentylsulfonyl-o-phenylenediamine 5-(4-bromobenzoyl)-N¹-cyclohexylsulfonyl-o-phenylenediamine
N¹-cycloheptylsulfonyl-5-(4-iodobenzoyl)-o-phenylenediamine
5-(3-nitrobenzoyl)-N¹-phenylsulfonyl-o-phenylenediamine
N¹-(2-furylsulfonyl)-5-(4-trifluoromethylbenzoyl)-o-phenylenediamine
5-benzoyl-N¹-(3-thienylsulfonyl)-o-phenylenediamine
5-(3,5-diethylbenzoyl)-N¹-(thiazol-2-ylsulfonyl)-o-phenylenediamine
N¹-(2-acetamido-4-methylthiazol-5-ylsulfonyl)-5-(2,4-dipropoxybenzoyl)-o-phenylenediamine
5-(2,6-dichlorobenzoyl)-N¹-(1,3,4-thiadiazol-2-ylsulfonyl)-o-phenylenediamine
5-(2,5-dibromobenzoyl)-N¹-(2-methyl-1,3,4-thiadiazol-5-ylsulfonyl)-o-phenylenediamine
N¹-dimethylaminosulfonyl-5-(3,5-dinitrobenzoyl)-o-phenylenediamine
5-[2,4-bis(trifluoromethyl)benzoyl]-N¹-methylpropylaminosulfonyl-o-phenylenediamine
5-(3-butoxy-5-butylbenzoyl)-N¹-ethylisopropylaminosulfonyl-o-phenylenediamine
5-(4-chloro-2-ethylbenzoyl)-N¹-pyrrolidinosulfonyl-o-phenylenediamine
5-(4-chloro-3-propoxybenzoyl)-N¹-piperidinosulfonyl-o-phenylenediamine
5-(5-bromo-2-isopropylbenzoyl)-N¹-morpholinosulfonyl-o-phenylenediamine
5-(3-bromo-5-chlorobenzoyl)-N¹-isopropylsulfonyl-o-phenylenediamine
N¹-neopentylsulfonyl-5-(3-nitro-4-trifluoromethylbenzoyl)-o-phenylenediamine
5-(2-chloro-4-nitrobenzoyl)-N¹-(1-ethylpropylsulfonyl)-o-phenylenediamine
5-(2-bromo-4-trifluoromethylbenzoyl)-N¹-s-butylsulfonyl-o-phenylenediamine
5-acetyl-N¹-dimethylaminosulfonyl-o-phenylenediamine
N¹-ethylmethylaminosulfonyl-5-propionyl-o-phenylenediamine
N¹-s-butylsulfonyl-5-(2-methylpropionyl)-o-phenylenediamine
N¹-isopropylsulfonyl-5-(2,2-dimethylpropionyl)-o-phenylenediamine
N¹-t-butylsulfonyl-5-hexanoyl-o-phenylenediamine
5-(3,3-dimethylbutyryl)-N¹-methylpropylamino-o-phenylenediamine
5-heptanoyl-N¹-pyrrolidinosulfonyl-o-phenylenediamine
N¹-cyclopropylsulfonyl-5-(3-ethyl-2-methylvaleryl)-o-phenylenediamine
5-(2,2-dimethylvaleryl)-N¹-isopropylsulfonyl-o-phenylenediamine
N¹-isobutylsulfonyl-5-(3-ethylhexanoyl)-o-phenylenediamine
N¹-(1-methylbutylsulfonyl)-5-(2-methylheptanoyl)-o-phenylenediamine
N¹-dimethylaminosulfonyl-5-octanoyl-o-phenylenediamine
5-(2-ethylvaleryl)-N¹-diethylaminosulfonyl-o-phenylenediamine
5-cyclopropylcarbonyl-N¹-isopropylsulfonyl-o-phenylenediamine
5-cyclobutylcarbonyl-N¹-morpholinosulfonyl-o-phenylenediamine
5-cyclohexylcarbonyl-N¹-phenylsulfonyl-o-phenylenediamine
5-cycloheptylcarbonyl-N¹-cyclohexylsulfonyl-o-phenylenediamine
5-cyclopropylacetyl-N¹-piperidinosulfonyl-o-phenylenediamine
5-cyclopentylacetyl-N¹-dimethylaminosulfonyl-o-phenylenediamine
5-cycloheptylacetyl-N¹-cyclopentylsulfonyl-o-phenylenediamine
N¹-t-butylsulfonyl-5-(2-cyclopropylpropionyl)-o-phenylenediamine
5-(2-cyclobutylpropionyl)-N¹-methylsulfonyl-o-phenylenediamine
5-(2-cycloheptylpropionyl)-N¹-propylsulfonyl-o-phenylenediamine
5-benzylcarbonyl-N¹-isopropylsulfonyl-o-phenylenediamine It will be understood that the above products where the 5-position group is other than a benzoyl group are also new compounds of this invention.

The 4-acyl-o-phenylenediamines which are the starting compounds for the present process are known compounds and chemists can obtain them at will. The Paget et al. patent discussed above gives some discussion of their synthesis, at column 8.

The selective sulfonation of this invention is unexpectedly easy to carry out. The phenylenediamine is merely contacted with the appropriate sulfonyl bromide or chloride, preferably the chloride, in any convenient solvent in the presence of at least about 1 mole of a pyridine base chosen from pyridine, the lutidines and the picolines, preferably pyridine.

The sulfonyl halides are readily obtained or prepared. The amount of the sulfonyl halide used in the reaction is of some importance. It has been observed that the use of a substantial excess of sulfonyl halide is likely to produce the undesired bissulfonyl compound, or the wrong mono-sulfonyl compound. Accordingly, only a modest excess of sulfonyl halide should be used, to assure that the phenylenediamine is fully consumed. It is preferred to use an amount of the sulfonyl halide from about 1 to about 1.2 mole per mole of the phenylenediamine, most preferably from about 1 to about 1.1 mole.

The type of organic solvent is not critical to the success of the process. The choice of solvent, of course, is intimately linked with the desired temperature of operation, and with the concentration at which the reaction is to be run. The best solvents for the process are the halogenated alkanes, such as chloroform, dichloromethane, 1,2-dichloroethane and the like. Dichloromethane is a particularly preferred solvent. Other types of solvents, however, including aromatics, halogenated aromatics, esters, amides and nitriles may be used as is convenient. Aromatics, such as benzene, toluene and the xylenes, should be used only when the concentration of the reactants is to be low, because their solvency for the starting compound is not great. Esters such as ethyl acetate, ethyl formate, propyl acetate and the like are useful solvents, as are nitriles such as acetonitrile and propionitrile.

It is also entirely possible to use a sufficient amount of pyridine base to dissolve the reactants and operate without any other solvent. Such operation is not preferred, because of the difficulty of handling the basic wastes after the process is completed.

The process is run in the presence of at least about 1 mole of pyridine base per mole of phenylenediamine. It is preferred to use at least about 2 moles of the pyridine base, and still more preferred to use from about 4 to about 10 moles of the pyridine base per mole of phenylenediamine. Greater amounts of pyridine base may be used as desired. In general, it is found that the yield of the desired sulfonation product tends to increase slowly with greater amounts of the pyridine base in the reaction mixture, and so the choice of the optimum amount of the pyridine base for a given process depends upon the relative costs of the pyridine base, compared to the other reactants, at the time and place in question.

The contrast of this process with similar processes run without a pyridine base is remarkable. When other inorganic or organic bases are used, the yield of sulfonated products is only in the range of about 10%, and about equal amounts of the possible isomers are produced.

The process is most preferably carried out at about the ambient temperature, which is considered to be from about 15° to about 35°. It may also be carried out effectively at temperatures in the preferred range from about 0° to about 50°, and temperatures in a range from about 0° to about 100° may be used if desired in the circumstances. In general, it is observed that elevated temperatures tend to produce more of the undesired isomeric product, where the sulfonyl has added to the amino group para to the acyl group. However, operation even at elevated temperatures gives a substantial yield of the desired isomer.

The most preferred product of the process of this invention is 5-benzoyl-$N^1$-isopropylsulfonyl-o-phenylenediamine, because of the exceptional antiviral activity of the benzimidazole formed from that compound.

Further preferred products of the process of this invention include those compounds described by the following partial definitions. It will be understood that the definitions below may be combined to form additional, narrower preferred classes.
(a) R is phenyl;
(b) R is mono-substituted-phenyl;
(c) R is phenyl mono-substituted with chloro, $C_1$-$C_4$ alkyl or $C_1$-$C_4$ alkoxy;
(d) R is 4-alkoxyphenyl;
(e) $R^1$ is $C_1$-$C_5$ alkyl;
(f) $R^1$ is $C_3$-$C_5$ branched alkyl;
(g) $R^1$ is isopropyl;
(h) $R^1$ is $C_3$-$C_7$ cycloalkyl;
(i) $R^1$ is phenyl;
(j) $R^1$ is thienyl.

Preferred novel compounds of this invention include those described by the following limitations, which may be combined as mentioned above.
(a) $R^4$ is alkyl;
(b) $R^4$ is $C_1$-$C_4$ alkyl;
(c) $R^4$ is cycloalkyl;
(d) $R^4$ is $C_5$-$C_6$ cycloalkyl;
(e) $R^1$ is $C_1$-$C_5$ alkyl;
(f) $R^1$ is $C_3$-$C_5$ branched alkyl;
(g) $R^1$ is isopropyl;
(h) $R^1$ is $C_3$-$C_7$ cycloalkyl;
(i) $R^1$ is phenyl;
(j) $R^1$ is thienyl.

The antiviral benzimidazoles are prepared from the products of the present process by the usual synthetic methods, especially by reaction with cyanogen bromide to form the 2-aminobenzimidazoles, which are a particularly preferred class of the antiviral compounds. See the Paget et al. patent, column 8. It is particularly advantageous to form the benzimidazoles by forming the sodium salt of the product of this process, as by contact with concentrated aqueous sodium hydroxide, removing the water and adding cyanogen bromide, which forms the benzimidazole upon stirring at ambient temperature.

The following examples are given to assure that a chemist who reads this document can fully understand the nature of the invention, and can carry it out to prepare products of his choice. In all cases, the desired isomeric sulfonated product and the undesired ones have different melting points and different retention times on high performance liquid chromatography (HPLC) columns, and can easily be recognized. The amounts of products given in the examples below, therefore, are known to be amounts of the desired isomer. In some cases, the amounts of the other isomer were analytically determined and are indicated. The preferred chromatographic analytical method is run by using a $C_{18}$ reverse phase column, and eluting with aqueous methanol at about 5.6 kg./cm$^2$. In all cases studied, the desired isomer came off the column before the undesired 4-isomer.

EXAMPLE 1

5-benzoyl-$N^1$-isopropylsulfonyl-o-phenylenediamine

Twenty g. of 4-benzoyl-o-phenylenediamine was suspended in 150 ml. of dichloromethane and 30 ml. of pyridine, and 11 ml. of isopropylsulfonyl chloride was added dropwise while the temperature of the mixture was held between 25° and 30°. The mixture was then stirred about 24 hours at 25°, and was washed with 150 ml. of 2N hydrochloric acid. The organic layer was then extracted with 190 ml. of 0.6N sodium hydroxide, and 100 ml. of isopropanol was added to the aqueous phase. The pH of the aqueous layer was adjusted to about 7.0 with concentrated hydrochloric acid, and the mixture was heated to reflux. The mixture was then stirred while it cooled overnight to 25°. It was then filtered and the solids were washed with 60 ml. of 33% aqueous isopropanol. The solids were dried in a vacuum oven at 50° for 8 hours to obtain 20.2 g. of the desired product, m.p. 150°-152°. High performance liquid chromatographic analysis indicated that the product was 98+% pure, showing a yield of 67.4% of the theoretical yield. The product was identified by its mass spectroscopic molecular ion, having a weight of 318, and by nuclear magnetic resonance (NMR) analysis on a 60-mHz instrument in CDCl$_3$ plus DMSOd$_6$, showing characteristic peaks at $\delta$1.3–1.4 (d, 6H, (CH$_3$)$_2$); 2.9–3.5 (m, 1H, CH), 5.5 (s, 2H, NH$_2$); 6.7–7.8 (m, 9H, aromatic).

EXAMPLE 2

5-benzoyl-$N^1$-methylsulfonyl-o-phenylenediamine

Ten g. of 4-benzoyl-o-phenylenediamine was combined with 75 ml. of dichloromethane and 15 ml. of pyridine and 3.8 ml. of methylsulfonyl chloride was added slowly while the temperature was held below 30°. The mixture was then stirred for 4 hours at 25°, and was worked up by washing with 75 ml. of 2N hydrochloric acid, and then extracting the organic layer with 100 ml. of 0.6N sodium hydroxide. The aqueous layer was neutralized to pH 7.0–7.5 with concentrated hydrochloric acid, and was extracted with ethyl acetate. The organic extract was evaporated to dryness under vacuum to obtain 11.9 g. of a crude product which was found to contain more than 90% of the desired isomer.

The product was recrystallized from 35 ml. of methanol and 110 ml. of toluene to obtain 6.3 g. of 99% pure product, m.p. 184°–186°. The calculated yield, based on the analysis of the crude product, was 87.5% of theoretical, and the purified isolated yield was 46.2% of theoretical. The product's identity was confirmed by its molecular ion of 290, and by NMR analysis, run as described in Example 1: δ2.93 (s, 3H, CH$_3$); 5.1 (s, 2H, NH$_2$); 6.7–7.7 (m, 9H, aromatic).

EXAMPLE 3

5-benzoyl-N$^1$-(2-thienylsulfonyl)-o-phenylenediamine

Ten g. of 4-benzoyl-o-phenylenediamine was slurried in 75 ml. of dichloromethane and 15 ml. of pyridine, and to it was added 9 g. of 2-thienylsulfonyl chloride. A mild exotherm occurred and the reaction mixture became a deep red solution. The mixture was stirred for 24 hours, and to it was added 75 ml. of 2N hydrochloric acid. The mixture was poured into 200 ml. of water, and the solids were filtered off and dried to obtain 16.75 g., 99% of theoretical, of crude product which was found to be more than 90% pure by HPLC analysis. A portion of the product was recrystallized from methanol and was found to have a melting point of 183°–186°. The product's identity was confirmed by its molecular ion of 358, and by its NMR spectrum, run as described above: δ5.4 (s, 2H, NH$_2$); 6.7–7.7 (m, 11H, aromatic and thienyl).

EXAMPLE 4

5-benzoyl-N$^1$-dimethylaminosulfonyl-o-phenylenediamine

Ten g. of 4-benzoyl-o-phenylenediamine was suspended in 75 ml. of dichloromethane and 15 ml. of pyridine at 15°. To the mixture was added 5.3 ml. of dimethylsulfamoyl chloride in one portion, and the reaction mixture was stirred at 25° for 20 hours. The pH was then adjusted to 2.0 with 2N hydrochloric acid, and the organic layer was separated and washed with 200 ml. of water. It was then extracted with 80 ml. of 0.75N sodium hydroxide solution, and the aqueous layer was neutralized to pH 7.1 with hydrochloric acid. It was then extracted with dichloromethane, and the organic extract was concentrated under vacuum and the residue was triturated with diethyl ether. A total of 10.5 g. of crude product was collected, corresponding to a crude yield of 69.6% of theoretical. Analysis of the crude product by HPLC indicated that it contained more than 90% of the desired isomer. The product was recrystallized from 60 ml. of isopropanol to obtain 8.76 g. of pure product, m.p. 147°–149°, a yield of 58.2% of theoretical. Its identity was confirmed by NMR analysis, run as described above: δ4.4 (s, 6H, (CH$_3$)$_2$); 5.3 (s, 2H, NH$_2$); 6.6–7.7 (m, 8H, aromatic); 8.5 (s, 1H, NH); and by mass spectroscopy, which showed a molecular ion of weight 319.

EXAMPLE 5

5-propionyl-N$^1$-isopropylsulfonyl-o-phenylenediamine

A 2.46 g. portion of 4-propionyl-o-phenylenediamine was suspended in 50 ml. of dichloromethane and 4.8 ml. of pyridine at 25°, and 1.8 ml. of isopropylsulfonyl chloride was added. The mixture was stirred at 25° for about 24 hours, and 70 ml. of 1.2N hydrochloric acid was added. The organic layer was separated and washed with 80 ml. of water, and was then extracted with 60 ml. of 0.4N sodium hydroxide. The aqueous layer was neutralized to pH 7.2 with hydrochloric acid, and was extracted with dichloromethane. The organic extract was concentrated under vacuum to obtain 2.6 g. of oil, which was found by HPLC analysis to contain more than 90% of the desired product. The crude yield was 65.2% of theoretical. Thirty ml. of diethyl ether was added, the mixture was heated to reflux and enough dichloromethane was added to dissolve all of the residue. The solution was cooled and 1.54 g. of 98% pure product was obtained by crystallization. Its melting point was 104°–106°, and the purified yield was 38% of theoretical. The product was identified by NMR analysis, run in CDCl$_3$ on a 60-mHz instrument: δ1.13 (t, 3H, CH$_3$); 1.4 (d, 6H, (CH$_3$)$_2$); 2.8 (q, 2H, CH$_2$); 3.3 (m, 1H, CH); 4.9 (s, 2H, NH$_2$); 6.67 (d, 1H, aromatic); 7.0 (s, 1H, NH); 7.5–7.8 (m, 2H, aromatic); and by mass spectroscopy, which showed a molecular ion of weight 270.

EXAMPLE 6

5-cyclohexylcarbonyl-N$^1$-isopropylsulfonyl-o-phenylenediamine

A 8.7 g. portion of 4-cyclohexylcarbonyl-o-phenylenediamine was dissolved in 75 ml. of dichloromethane and 15 ml. of pyridine. To it was added 4.8 ml. of isopropylsulfonyl chloride while the temperature was held between 25° and 30°. The mixture was then stirred overnight, and to it was added 75 ml. of 2N hydrochloric acid and the mixture was stirred for 30 minutes. The aqueous layer was then washed with about 25 ml. of dichloromethane, and the organic layer was added to the first organic layer. To the combined organics was added 90 ml. of 0.7N sodium hydroxide solution, and to the aqueous layer was added 50 ml. of isopropanol and its pH was adjusted to about 7. The mixture was stirred overnight, and was extracted with 250 ml. of dichloromethane.

The product of this example was identified by converting it to the corresponding benzimidazole.

PREPARATION 1

2-amino-6-cyclohexylcarbonyl-1-isopropylsulfonylbenzimidazole

To the extract obtained above was added 6.72 g. of 50% aqueous sodium hydroxide, and the water was removed from the mixture by azeotropic distillation. The mixture was then cooled to ambient temperature, and 4.8 g. of cyanogen bromide was added. The mixture was stirred at ambient temperature for 2 days, and then the dichloromethane was distilled off and replaced with 120 ml. of methanol. The mixture was stirred under reflux for 3 hours, and was then chilled in an ice bath for 3 hours. The mixture was then concentrated under vacuum to a solid residue, which was dissolved in hot toluene. The mixture was chilled and cooled until a precipitate formed, which was identified as 8.4 g. of 2-amino-6-cyclohexylcarbonyl-1-isopropylsulfonylbenzimidazole. The product was identified by its NMR spectrum, run on a 60-mHz instrument: δ1.25 (d, 6H, (CH$_3$)$_2$); 2–1 (m, 11H, cyclohexyl).

EXAMPLE 7

5-benzoyl-N$^1$-isopropylsulfonyl-o-phenylenediamine

Ten g. of 4-benzoyl-o-phenylenediamine was combined with 85 ml. of dichloromethane and 4 ml. of pyridine, and the mixture was cooled to 20°. To the mixture was added 5.5 ml. of isopropylsulfonyl chloride in one portion, and it was then stirred at ambient temperature for 20 hours. To it was added 75 ml. of water, and the aqueous phase was then washed with a small amount of dichloromethane, which was combined with the original organic layer. The organic mixture was then extracted with 70 ml. of 0.9N sodium hydroxide, and 20 ml. of additional water was added to the aqueous phase. Forty ml. of isopropanol was added to the aqueous phase and its pH was adjusted to 7.2 with hydrochloric acid. The mixture was then stirred for one and one-half hours at ambient temperature and then in an ice bath for 2 hours. It was then filtered and the solids were washed with 30 ml. of 33% aqueous isopropanol and dried to obtain 6.9 g. of the desired product, which was 86.2% pure by HPLC analysis and contained 9.7% of the undesired isomer. The corrected yield was 39.8% of theoretical.

EXAMPLE 8

5-benzoyl-$N^1$-isopropylsulfonyl-o-phenylenediamine

A mixture of 20 g. of 4-benzoyl-o-phenylenediamine, 165 ml. of dichloromethane and 15 ml. of pyridine was cooled to 5°. To it was added 11 ml. of isopropylsulfonyl chloride in one portion, and the mixture was stirred at constant temperature for 5 hours and then overnight at 25°. To the mixture was then added 150 ml. of 2N hydrochloric acid, and the mixture was stirred for 1 hour at ambient temperature. It was then filtered, the solids were washed with dichloromethane, and the aqueous layer of the combined filtrate was separated and washed with 30 ml. of dichloromethane. The combined organic layers were extracted with 170 ml. of 0.7N sodium hydroxide, and the aqueous layer was adjusted to 190 ml. volume by adding water. To it was added 100 ml. of isopropanol, and its pH was then adjusted to 7.0-7.5 with concentrated hydrochloric acid. The mixture was stirred for 90 minutes at ambient temperature, then in an ice bath for two and one-half hours. It was then filtered, and the solids were washed with 33% aqueous isopropanol and dried. The product was 18.3 g. of the desired product, found to be 96.0% pure by HPLC analysis and containing 2.5% of the undesired 4-benzoyl-$N^1$-isopropylsulfonyl-o-phenylenediamine. The corrected yield of the desired product, substantially identical to the product of Example 1, was 58.7% of the theoretical yield.

EXAMPLE 9

5-benzoyl-$N^1$-isopropylsulfonyl-o-phenylenediamine

A 20 g. portion of 4-benzoyl-o-phenylenediamine was dissolved in 143 ml. of dichloromethane and 37.5 ml. of pyridine and cooled to 5°. To the mixture was added 11 ml. of isopropylsulfonyl chloride in one portion, and the reaction was carried out and the product isolated as was described in Example 5 to obtain 24.6 g. of the desired product, which was 86.9% pure by HPLC analysis, containing 11.6% of the undesired 4-benzoyl isomer. The corrected yield was 71.2% of the theoretical yield.

EXAMPLE 10

5-benzoyl-$N^1$-isopropylsulfonyl-o-phenylenediamine

Twenty g. of 4-benzoyl-o-phenylenediamine was dissolved in 120 ml. of dichloromethane and 60 ml. of pyridine and cooled to 5°. To the mixture was added 11 ml. of isopropylsulfonyl chloride in one portion, and the reaction was then carried out and the product isolated as described in Example 5 above. The product was 24.7 g. of the desired product, found to be 93.2% pure by HPLC analysis and containing 5.7% of the undesired 4-benzoyl isomer. The corrected yield was 76.7% of the theoretical yield.

EXAMPLE 11

5-benzoyl-$N^1$-isopropylsulfonyl-o-phenylenediamine

A 5.02 g. portion of 4-benzoyl-o-phenylenediamine was combined with 100 ml. of toluene and 15 ml. of pyridine, and 2.25 ml. of isopropylsulfonyl chloride was added. The mixture was stirred overnight at ambient temperature. To it was added 75 ml. of 2N hydrochloric acid, and the mixture was stirred for 20 minutes. One hundred ml. of ethyl acetate was added, and the organic layer was separated. The solvents were removed under vacuum to obtain an oil, which was dissolved in dichloromethane and mixed with 30 ml. of 1N sodium hydroxide. The 2-phase mixture was stirred for 30 minutes, and the aqueous layer was separated and made acid with 2N hydrochloric acid. The acid mixture was then extracted with dichloromethane, and the organic layer was evaporated under vacuum to obtain a gummy solid, which was recrystallized from 25 ml. of isopropanol and 80 ml. of water, with cooling. The solids were recovered by filtration and washed with 33% aqueous isopropanol. After drying, the product was 2.4 g. of the desired product, 96.5% pure by HPLC analysis, containing 0.65% of the 4-benzoyl isomer. The yield was 31.2% of the theoretical yield; the low solvency of toluene is believed to be the reason for the relatively low yield.

EXAMPLE 12

5-benzoyl-$N^1$-isopropylsulfonyl-o-phenylenediamine

Four g. of 4-benzoyl-o-phenylenediamine was dissolved in 45 ml. of pyridine, and 2.3 ml. of isopropylsulfonyl chloride was added dropwise while the temperature rose from 23° to 30°. The mixture was stirred for 2 hours at ambient temperature, and then 60 ml. of ethyl acetate was added to it. To it was then added 100 ml. of 4N hydrochloric acid, and the layers were separated. The organic layer was washed with 200 ml. of water, then with 100 ml. of 1N hydrochloric acid, then with saturated sodium chloride solution, and finally with potassium carbonate solution. All of the aqueous washes were extracted with small portions of ethyl acetate, and all the organic layers were then combined and dried over sodium sulfate. The ethyl acetate was removed under vacuum, isopropanol was added to the residue and it was removed under vacuum. Then the residue was dissolved in 30 ml. of isopropanol with heating, and 60 ml. of water was slowly added with heating. The mixture was cooled, seeded with small crystals of the desired product, chilled in an ice bath and filtered. The solids were washed with 33% isopropanol, and the product was dried under vacuum to obtain 3.8 g. of the desired product, which was 96.2% pure by HPLC analysis and contained 2.0% of the undesired 4-benzoyl isomer. The yield was 60.7% of theoretical.

EXAMPLE 13

5-benzoyl-$N^1$-isopropylsulfonyl-o-phenylenediamine

Five g. of 4-benzoyl-o-phenylenediamine was dissolved in 45 ml. of acetonitrile and 7.5 ml. of pyridine, and the mixture was cooled to 10°. A 2.25 ml. portion of isopropylsulfonyl chloride was added in one portion, and the mixture was then stirred for 16 hours at ambient temperature. The mixture was then evaporated under vacuum to an oily residue, and 75 ml. of 0.7N hydrochloric acid was added, together with 50 ml. of dichloromethane. An intractable emulsion formed, which was broken by adding a small amount of ethyl acetate and adjusting the pH of the mixture to about 8 with 4N sodium hydroxide. The organic layer was evaporated to a gum, and to it was added 60 ml. of 0.7N sodium hydroxide, and the mixture was heated on the steam bath for 10 minutes and then cooled. The insoluble matter was filtered off, and the filtrate was extracted with 100 ml. of dichloromethane. The basic aqueous layer was neutralized to pH 7 with concentrated hydrochloric acid, and then extracted with dichloromethane. The solvent was removed from the extract under vacuum to obtain a gummy solid, which was dried in the vacuum oven for 2 hours. The crude weight of the product was 5.30 g., a crude yield of 70.6% of theoretical. HPLC analysis showed less than 10% of the 4-benzoyl isomer in the crude product.

EXAMPLE 14

5-benzoyl-$N^1$-isopropylsulfonyl-o-phenylenediamine

Five g. of 4-benzoyl-o-phenylenediamine was dissolved in 40 ml. of ethyl acetate and 7.5 ml. of pyridine, and the solution was cooled to 10°. To it was added 2.25 ml. of isopropylsulfonyl chloride in 1 minute, and the ice bath was then removed and the mixture was stirred at ambient temperature overnight. To it was then added 40 ml. of 2N hydrochloric acid, and the layers were separated. The organic layer was then evaporated under vacuum to obtain about 5.6 g. of a dark solid, which was mixed with 100 ml. of 0.8N sodium hydroxide and heated on the steam bath for 10 minutes. The mixture was then cooled and filtered, and the filtrate was extracted with dichloromethane. To the aqueous layer was added concentrated hydrochloric acid to pH 7, and the acid solution was extracted with 100 ml. of dichloromethane. The organic layer was evaporated under vacuum to obtain 4.3 g. of a gummy solid, which was dried for 2 hours under vacuum. HPLC analysis of the crude product showed that it contained less than 10% of the undesired 4-benzoyl isomer. The crude yield of the desired product was 56.8% of theoretical.

EXAMPLE 15

5-benzoyl-$N^1$-isopropylsulfonyl-o-phenylenediamine

Ten g. of 4-benzoyl-o-phenylenediamine was dissolved in 75 ml. of tetrahydrofuran and 15 ml. of pyridine and the solution was cooled to 20°. To it was added 5.5 ml. of isopropylsulfonyl chloride in one portion, and the mixture was stirred overnight at ambient temperature. To it was then added 75 ml. of 2N hydrochloric acid, and the mixture was stirred for 10 minutes. The aqueous layer was removed and washed with 40 ml. of tetrahydrofuran, and the combined organics were washed with 100 ml. of water and 50 ml. of saturated sodium chloride solution. The organic layer was then removed and evaporated under vacuum, and 75 ml. of dichloromethane was added to the residue. To it was then added 75 ml. of 0.8N sodium hydroxide, and the mixture was stirred for 30 minutes. The organic layer was then washed with 50 ml. of water, and the combined aqueous layers were adjusted to pH 7.5 with concentrated hydrochloric acid. The mixture was then extracted with dichloromethane, and the organic extract was dried over magnesium sulfate and evaporated under vacuum to an oil. Isopropyl alcohol was added to the oil, and was evaporated away under vacuum. To the residue was then added 150 ml. of 33% isopropanol, and the mixture was heated and then cooled slowly to about 15°. The mixture was then filtered and the solids were washed with 90 ml. of 33% aqueous isopropanol and dried to obtain 6.65 g. of the desired product, m.p. 155°–157°, which was 99.55% pure by HPLC analysis. The yield was 44.5% of theoretical.

EXAMPLE 16

5-benzoyl-$N^1$-isopropylsulfonyl-o-phenylenediamine

Studies were carried out to determine the optimum reaction time at various temperatures. The reaction mixtures contained 10 g. of 4-benzoyl-o-phenylenediamine, 75 ml. of dichloromethane, 15 ml. of pyridine and 5.5 ml. of isopropylsulfonyl chloride. However, the 86° study was carried out with 1,2-dichloroethane as the solvent instead of dichloromethane. Samples were withdrawn from the reaction mixture at hourly or 2-hourly intervals up to 8 hours and then at 24 hours, and the samples were analyzed by HPLC to determine the approximate amount of the desired product present. Before analysis, the 2.5-ml. samples were mixed with 2 ml. of diethylamine and 20 ml. of dichloromethane, and the solvents were removed from the sample under vacuum. The residue was then dissolved in ethyl acetate, and the insolubles were filtered off. The ethyl acetate was then removed under vacuum, a small amount of methanol was added to the residue and removed under vacuum, and then 20 ml. of methanol was added to the residue to prepare the analytical sample.

At 25°, it was found that the maximum yield of the desired product was obtained at 24 hours, but that the 8-hour yield was very close to optimum. The amount of the undesired 4-benzoyl isomer did not increase as the reaction went on, but reached its maximum at about 3 hours and did not change appreciably thereafter.

At 45°, the yield of the desired product appeared to be optimum at about 6 hours. Again, the amount of the undesired isomer was small and did not increase after about 3 hours reaction time.

At 86°, the optimum reaction time was about 2 hours, and the amount of the undesired isomer, compared to the amount of product, was relatively high.

We claim:

1. A compound of the formula

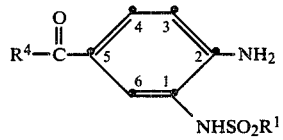

wherein
R$^4$ is $C_1$–$C_7$ alkyl, $C_3$–$C_7$ cycloalkyl, $C_3$–$C_7$ cycloalkylmethyl, 1-($C_3$–$C_7$ cycloalkyl)ethyl or benzyl;
R$^1$ is $C_1$–$C_5$ alkyl or $C_3$–$C_7$ cycloalkyl.

2. A compound of claim 1 wherein R$^1$ is isopropyl.

3. A compound of claim 1 wherein R$^1$ is $C_3$–$C_5$ branched alkyl.

4. A compound of claim 1 wherein R$^4$ is cycloalkyl.

* * * * *